United States Patent
de la Guardia et al.

(10) Patent No.: US 11,224,559 B2
(45) Date of Patent: Jan. 18, 2022

(54) COMPOSITIONS AND METHODS FOR REMOVING HAIR STYLING AIDS

(71) Applicant: Strength of Nature, LLC, Atlanta, GA (US)

(72) Inventors: Mario M. de la Guardia, Duluth, GA (US); Tony Ray Adair, Daphne, AL (US)

(73) Assignee: Strength of Nature, LLC, Atlanta, GA (US)

( * ) Notice: Subject to any disclaimer, the term of this patent is extended or adjusted under 35 U.S.C. 154(b) by 821 days.

(21) Appl. No.: 15/397,298

(22) Filed: Jan. 3, 2017

(65) Prior Publication Data
US 2017/0340535 A1  Nov. 30, 2017

Related U.S. Application Data

(63) Continuation of application No. 11/683,818, filed on Mar. 8, 2007, now Pat. No. 9,532,936.

(51) Int. Cl.
*A61Q 5/02* (2006.01)
*A61K 8/34* (2006.01)
*A61K 8/37* (2006.01)

(52) U.S. Cl.
CPC ............... *A61K 8/34* (2013.01); *A61K 8/345* (2013.01); *A61K 8/37* (2013.01); *A61Q 5/02* (2013.01)

(58) Field of Classification Search
None
See application file for complete search history.

(56) References Cited

U.S. PATENT DOCUMENTS

| | | | |
|---|---|---|---|
| 5,139,786 A | 8/1992 | Ferrini et al. | |
| 5,750,122 A * | 5/1998 | Evans | A61Q 5/02 424/401 |
| 6,649,579 B2 * | 11/2003 | Denton | A61K 8/361 510/138 |
| 9,532,936 B2 | 1/2017 | de la Guardia, Jr. et al. | |
| 2002/0122782 A1 | 9/2002 | Bichard | |
| 2004/0185026 A1 * | 9/2004 | Pantini | A61K 8/86 424/70.23 |
| 2004/0229762 A1 | 11/2004 | Rutter | |
| 2005/0137102 A1 * | 6/2005 | Shoaf | C11D 3/188 510/138 |
| 2005/0214239 A1 | 9/2005 | Nojiri et al. | |
| 2005/0281755 A1 | 12/2005 | Zarif et al. | |
| 2006/0093567 A1 * | 5/2006 | Tsuji | A61Q 7/02 424/70.14 |
| 2007/0141007 A1 * | 6/2007 | Glynn, Jr. | A61K 8/70 424/70.11 |

OTHER PUBLICATIONS

Requirement for Restriction/Election was issued on Sep. 10, 2010 by the USPTO for U.S. Appl. No. 11/683,818, filed Mar. 8, 2007 and granted as U.S. Pat. No. 9,532,936 on Jan. 3, 2017 (Inventor—Mario M. de la Guardia, et al.) (7 pages).
Response to Requirement for Restriction/Election dated Mar. 10, 2011 to the USPTO for U.S. Appl. No. 11/683,818, filed Mar. 8, 2007 and granted as U.S. Pat. No. 9,532,936 on Jan. 3, 2017 (Inventor—Mario M. de la Guardia, et al.) (3 pages).
Non Final Rejection dated May 31, 2011 by the USPTO for U.S. Appl. No. 11/683,818, filed Mar. 8, 2007 and granted as U.S. Pat. No. 9,532,936 on Jan. 3, 2017 (Inventor—Mario M. de la Guardia, et al.) (6 pages).
Response to Non Final Rejection dated Nov. 30, 2011 to the USPTO for U.S. Appl. No. 11/683,818, filed Mar. 8, 2007 and granted as U.S. Pat. No. 9,532,936 on Jan. 3, 2017 (Inventor—Mario M. de la Guardia, et al.) (12 pages).
Final Rejection dated Feb. 17, 2012 by the USPTO for U.S. Appl. No. 11/683,818, filed Mar. 8, 2007 and granted as U.S. Pat. No. 9,532,936 on Jan. 3, 2017 (Inventor—Mario M. de la Guardia, et al.) (11 pages).
Response to Final Rejection dated Aug. 17, 2012 to the USPTO for U.S. Appl. No. 11/683,818, filed Mar. 8, 2007 and granted as U.S. Pat. No. 9,532,936 on Jan. 3, 2017 (Inventor—Mario M. de la Guardia, et al.) (13 pages).
Non Final Rejection dated Dec. 21, 2012 by the USPTO for U.S. Appl. No. 11/683,818, filed Mar. 8, 2007 and granted as U.S. Pat. No. 9,532,936 on Jan. 3, 2017 (Inventor—Mario M. de la Guardia, et al.) (9 pages).
Response to Non Final Rejection dated Jun. 21, 2013 to the USPTO for U.S. Appl. No. 11/683,818, filed Mar. 8, 2007 and granted as U.S. Pat. No. 9,532,936 on Jan. 3, 2017 (Inventor—Mario M. de la Guardia, et al.) (21 pages).
Final Rejection dated Sep. 10, 2013 by the USPTO for U.S. Appl. No. 11/683,818, filed Mar. 8, 2007 and granted as U.S. Pat. No. 9,532,936 on Jan. 3, 2017 (Inventor—Mario M. de la Guardia, et al.) (10 pages).
Response to Final Rejection dated Oct. 10, 2014 to the USPTO for U.S. Appl. No. 11/683,818, filed Mar. 8, 2007 and granted as U.S. Pat. No. 9,532,936 on Jan. 3, 2017 (Inventor—Mario M. de la Guardia, et al.) (11 pages).
Final Rejection dated Oct. 23, 2014 by the USPTO for U.S. Appl. No. 11/683,818, filed Mar. 8, 2007 and granted as U.S. Pat. No. 9,532,936 on Jan. 3, 2017 (Inventor—Mario M. de la Guardia, et al.) (11 pages).
Response to Final Rejection dated Nov. 23, 2015 to the USPTO for U.S. Appl. No. 11/683,818, filed Mar. 8, 2007 and granted as U.S. Pat. No. 9,532,936 on Jan. 3, 2017 (Inventor—Mario M. de la Guardia, et al.) (11 pages).
Non Final Rejection dated Jan. 12, 2016 by the USPTO for U.S. Appl. No. 11/683,818, filed Mar. 8, 2007 and granted as U.S. Pat. No. 9,532,936 on Jan. 3, 2017 (Inventor—Mario M. de la Guardia, et al.) (11 pages).

(Continued)

*Primary Examiner* — Jyothsna A Venkat
(74) *Attorney, Agent, or Firm* — Ballard Spahr LLP

(57) ABSTRACT

Disclosed are compositions for solubilizing and/or removing a hair styling aid composition from hair. The compositions comprise at least one active solvent, wherein the active solvent is a glycol or an ester; and a carrier composition comprising a liquid vehicle. Also disclosed are methods for solubilizing and/or removing hair styling aids from hair.

2 Claims, No Drawings

(56) References Cited

OTHER PUBLICATIONS

Response to Non Final Rejection dated Jul. 12, 2016 to the USPTO for U.S. Appl. No. 11/683,818, filed Mar. 8, 2007 and granted as U.S. Pat. No. 9,532,936 on Jan. 3, 2017 (Inventor—Mario M. de la Guardia, et al.) (12 pages).
Notice of Allowance dated Aug. 19, 2016 by the USPTO for U.S. Appl. No. 11/683,818, filed Mar. 8, 2007 and granted as U.S. Pat. No. 9,532,936 on Jan. 3, 2017 (Inventor—Mario M. de la Guardia, et al.) (7 pages).
Notice of Allowance dated Aug. 30, 2016 by the USPTO for U.S. Appl. No. 11/683,818, filed Mar. 8, 2007 and granted as U.S. Pat. No. 9,532,936 on Jan. 3, 2017 (Inventor—Mario M. de la Guardia, et al.) (2 pages).
Issue Notification dated Dec. 14, 2016 by the USPTO for U.S. Appl. No. 11/683,818, filed Mar. 8, 2007 and granted as U.S. Pat. No. 9,532,936 on Jan. 3, 2017 (Inventor—Mario M. de la Guardia, et al.) (1 page).

* cited by examiner

COMPOSITIONS AND METHODS FOR REMOVING HAIR STYLING AIDS

CROSS REFERENCE TO RELATED APPLICATIONS

This application is a continuation of and claims the benefit of priority to co-pending U.S. patent application Ser. No. 11/683,818, filed Mar. 8, 2007. The entire disclosure of which is incorporated by reference herein for all purposes.

FIELD OF THE INVENTION

The present invention relates generally to the field of hair care products and, more particularly, to compositions and methods for solubilizing and/or removing hair styling aids that have been applied to hair.

BACKGROUND OF THE INVENTION

Among a wide variety of hair styling techniques used today, hair weaves are often chosen as a popular hair supplement for a particular styling regime. These weaves are typically either sown in by a stylist, "glued" in with resins, or, more often, attached to the existing hair and surrounding scalp with a latex rubber bonding agent. Subsequent removal of these weaves from hair is challenging as it causes painful hair pulling, hair damage, and even subsequent hair loss.

Commercially available hair bonding agent removers are generally limited to shampoos containing harsh detergent-type surfactants and/or irritating chemicals such as mineral spirits and kerosene. These shampoo products are marginally effective at softening the bonding material because the acceptable amount of the active chemical, i.e., the mineral spirits and/or kerosene, must be kept low in order to prevent excessive scalp irritation. Further, the surfactant/degreaser combination often dries out the hair, and even irritates the scalp. Oily materials such as mineral oil and various natural oils have also been used to remove bonding agents. However, these products must be left on the hair for long periods of time in order to obtain any noticeable effect on the bonding material. As such, neither of these current approaches yields satisfactory results as painful hair pulling, hair damage, hair loss, and scalp dryness and irritation are often associated with the use of these formulations.

In addition to hair weave bonding agents, a variety of hair styling aids containing resinous fixatives, such as gels, sprays, spritzes, and mousses, are also frequently used to maintain styled hair in a particular curl or configuration. The removal of resinous build up from the hair has also presented a challenge to the industry. In particular, the removal of the resinous styling product buildup from the hair is currently accomplished in one of two ways. One option is to utilize multiple applications of a "stripping" shampoo during which vigorous manipulation of the hair is used to forcibly break the adhesion between hair fibers and loosen the styling residue on individual hairs. Alternatively, a comb or brush is used to break the adhesions between hair fibers followed by multiple applications of a stripping shampoo and vigorous manipulation of the hair to loosen styling residues from individual hairs.

These so-called stripping shampoo products of the current art contain high loadings of harsh surfactants designed to act as detergents on the hair. Stripping shampoos are also formulated to have an alkaline pH (pH 8.0 to pH 10) to enhance their "detergency". The combination of alkaline pH and high surfactant loading can: 1) cause hair to swell which in turn causes lifting of the protective cuticle layer; 2) remove hairs natural protective/lubricating oils and moisturizing agents from the hair and the scalp; and 3) enhance the tangling effect created by the vigorous manipulation of the hair. The end results of the use of the stripping shampoos of the current art are that the hair is left in a swollen state with lifted cuticle edges, little or no remaining natural lubrication or moisturization, and severely tangled from the vigorous manipulation. Accordingly, both methods of removing resinous styling residues from the hair can create severe hair damage and can result in undesirable side-effects for the consumer.

Further, these stripping shampoos are not always effective at completely removing heavy styling aide build-up on the hair. The failure to completely and adequately remove the styling residue can 1) create increased drag during any subsequent combing caused by lifted prills of resin; 2) make the hair look as though there is residual dirt or debris on it; and 3) contribute to the consumer perception of "dandruff" because the loosened material subsequently falls from the hair onto the scalp and shoulders over time. The perception of dandruff then causes the consumer to use further harsh shampoo treatments in an attempt to eliminate the dandruff problem.

Even more damaging to the hair and scalp is the process whereby the consumer or salon professional attempts to "comb-out" the styling residues before shampooing. This method is recognized as a leading cause of hair breakage and scalp irritation/damage by both consumers and salon professionals alike but is often perceived as the only effective way to remove excessive styling residues from the hair.

Unfortunately, the current art limits the options available to persons seeking to apply subsequent treatments to hair that has been previously treated with a resinous fixative styling aid. For instance, persons who wish to use chemical treatments such as hair straighteners or curly perms are at a disadvantage when using the products available in the current art. Shampooing the hair and scalp to remove styling residues prior to applying hair straighteners or curly perms can cause these products to irritate or burn the scalp. This is especially true when the stripping shampoos of the current art are used. The manufacturers of hair straightening and curling products usually include a warning statement requiring the consumer to wait at least 24 to 48 hours after shampooing before subsequently applying the straightening or curling products. The consumer must either: (1) shampoo and wait, (2) shampoo and risk irritation by immediately using the straightener, or (3) not shampoo and attempt to brush the styling residues from the hair. Each of these options involves unnecessary risk to the health of the consumer's hair and scalp.

The current art also does not provide for a suitable means by which a consumer can efficiently re-arrange his or her hair from one style to another without having to remove a prior application of a styling aid. In particular, the current art does not offer an option of loosening a previous curl pattern, re-arranging the hair to another style, and locking the hair into place with additional fixative.

Accordingly, there is a need in the art for compositions that can, in one aspect, be used to remove hair bonding agents from hair and scalp without resulting in painful hair pulling, significant hair damage, significant hair loss, and scalp dryness and irritation. Additionally, there also is a need in the art for compositions that can solubilize resinous hair styling aids such that, in one aspect, the hair styling aid can be removed or, in another aspect, the styled hair can be restyled to a different curl configuration without requiring the removal of a prior application of a styling aid.

SUMMARY OF THE INVENTION

The present invention provides compositions and methods for solubilizing and/or removing hair styling aids, including for example, resinous fixatives and latex based hair-bonding agents.

In one aspect, the present invention provides a composition for removing a hair styling aid from hair. The composition comprises at least one active solvent, wherein the at least one active solvent is a glycol and/or an ester, and a carrier composition comprising a liquid vehicle. As described herein, the composition is suitable for applying to hair and removing a hair styling composition applied thereto.

In another aspect, the present invention provides a method for removing a hair styling agent from hair. The method comprises contacting hair that has a hair styling agent applied thereto with one or more applications of a styling agent remover for a time sufficient to solubilize the styling agent. In one aspect, the styling agent remover comprises at least one solvent, wherein the at least one active solvent is a glycol and/or an ester. After the application has remained in contact with the hair fora suitable period of time, the treated hair can be combed to disrupt or separate any two or more hairs that may be adhered by the hair styling agent. After combing, the solubilized styling agent can then be removed from the hair.

In another aspect, the present invention further provides a method for restyling hair having one or more styling agents previously applied thereto. The method according to this aspect can comprise contacting hair having a styling agent previously applied thereto with one or more applications of a styling agent remover for a time sufficient to solubilize the styling agent and to provide treated hair having the solubilized styling agent applied thereto. The hair having solubilized styling agent applied thereto can then be restyled into a desired configuration. After restyling, the solubilized styling agent can be at least substantially dried to secure the restyled hair in the desired configuration.

In still a further aspect, the present invention also provides a method of moisturizing and softening hair. The compositions of the present invention can be used to enhance the perception of resin-styled hair. This is can be accomplished by contacting resin-styled hair with the compositions of the present invention and allowing sufficient contact time for the composition to penetrate through the resin coating and into the hair fiber. This step can be followed by at least substantially drying the hair or the hair can be left to dry naturally.

The perception of enhanced hair softness can be accomplished by penetrating any existing resin coating with a hair softening/moisturizing agent without first having to remove the resin coating. The softening/moisturizing agent acts as a plasticizing agent to impart increased flexibility to the hair fiber. Likewise, the compositions of the current invention can be used on hair which does not have a resin coating but is in need of a softening/moisturizer treatment (e.g. beard hair). The treatment can in one aspect comprise a moisturizing treatment for resin-styled hair. In another aspect, the treatment can comprise softening coarse hair. The method comprises first providing hair in need of treatment. The hair can then be contacted with one or more applications of a treatment composition comprising i) at least one active solvent, wherein the at least one active solvent is a glycol or an ester; and ii) a carrier comprising a liquid vehicle. After the application of the treatment composition, the composition is allowed to remain in contact with the hair in need of treatment for a period of time sufficient to at least substantially penetrate the hair.

Additional embodiments of the invention will be set forth, in part, in the detailed description, and any claims that follow, and in part will be derived from the detailed description, or can be learned by practice of the invention. It is to be understood that both the foregoing general description and the following detailed description are exemplary and explanatory only and are not restrictive of the invention as disclosed.

DETAILED DESCRIPTION OF THE INVENTION

The following description of the invention is provided as an enabling teaching of the invention in its best, currently known embodiment. To this end, those skilled in the relevant art will recognize and appreciate that many changes can be made to the various embodiments of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

It must be noted that, as used in the specification and the appended claims, the singular forms "a," "an" and "the" include plural referents unless the context clearly dictates otherwise. Thus, for example, reference to a "glycol" includes mixtures of glycols.

Often ranges are expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

A weight percent of a component, unless specifically stated to the contrary, is based on the total weight of the formulation or composition in which the component is included.

By the term "effective amount" of a compound or property as provided herein is meant such amount as is capable of performing the function of the compound or property for which an effective amount is expressed. As will be pointed out below, the exact amount required will vary from process to process, depending on recognized variables such as the compounds employed and the processing conditions observed. For example, an effective amount of a solubilizing composition will depend, in part, on the amount and/or type of hair styling aid being solubilized, the strength of the solubilizer composition applied and the condition of the hair prior to application of the solubilizing agent. Thus, it is not possible herein to specify an exact "effective amount." However, an appropriate effective amount may be determined by one of ordinary skill in the art using only routine experimentation.

In a first aspect summarized above, the present invention provides compositions for solubilizing hair styling aids, such as latex bonding agents and resinous styling residues, which have been applied to hair. As will be set forth in more detail below, once solubilized, the styling agents can be removed from the hair or, alternatively, the hair having the solubilized styling aid applied thereon can be restyled and set to a desired configuration without the need to first remove a previous application of the styling aid.

The compositions of the present invention generally comprise at least one active solvent and a carrier and are further suitable for applying to hair to solubilize a hair styling composition that has been previously applied thereto. As used herein, the term "active solvent" refers to a solvent that is capable of at least partially dissolving styling residues, glues, and/or bonding agents to thereby disrupt or break the fixative bonds formed between two or more fibers. Suitable active solvents that can be used in the inventive compositions include one or more glycols, such as propylene glycol, dipropylene glycol, and tripropylene glycol. Additionally, in another aspect, the suitable active solvent includes one or more esters, such as methyl soyate. As shown in the Examples which follow, the aforementioned commercially available non-toxic solvents are effective for removing hair bonding agents like latex rubber and resinous styling residues from hair. Further, these solvents are listed on the GRAS (Generally Regarded As Safe) list published by the FDA and are considered non-toxic, non-irritating, and safe for use on skin and hair.

The amount of active solvent used in the composition of the present invention can range from 0.1 weight percent up to 85 weight percent based upon the total weight of the composition, including for example, such amounts as 5, 10, 15, 20, 25, 30, 35, 40, 45, 50, 55, 60, 65, 70, or even 75 weight percent. Still further, the active solvent can be present in an amount within any range derived from the aforementioned weight percentages. For example, the active solvent can be present in an amount in the range of from 5 to 85 weight percent, 15 to 85 weight percent, or even 15 to 60 weight percent. Still further, in an aspect comprising a plurality of active solvents, it should be understood that the plurality of active solvents can each be present in any amount or range of amounts such that the total weight percentage of the plurality of active solvents is in that range of from 0.1 weight percent up to 85 weight percent based upon the total weight of the composition.

In addition to the active solvent component, the compositions of the present invention further comprise a carrier comprised of at least one liquid vehicle. The liquid vehicle can in one aspect be water. Alternatively, in another aspect, the liquid vehicle can be selected from a lower (C1-C4) alkanol, including for example, ethanol or isopropanol. Likewise, the liquid vehicle can be comprised of blends of two or more liquid vehicles such as, for example, water and lower (C1-C4) alkanols. The liquid vehicle can also be present in any amount ranging from, for example, 15 weight percent up to 99.9 weight percent of the composition, including such exemplary amounts as 20, 25, 30, 35, 40, 45, 50, 55, 60, 65, 70, 75, 80, 85, 90, or 95 weight percent of the composition. The liquid vehicle can also be present in an amount within any range derived from the above mentioned values. Still further, in an aspect comprising a plurality of liquid vehicles, it should be understood that the plurality of liquid vehicles can each be present in any amount or range of amounts such that the total weight percentage of the plurality of liquid vehicles is in that range of from 15 weight percent up to 99.9 weight percent of the composition.

The carrier can also optionally comprise and one or more carrier additives. The carrier additives are optional components in the formulations that can be used to provide particularly desired physical and or chemical properties to the finished product. Additionally, these additives can also be used to provide additional therapeutic qualities to the compositions of the present invention. For example, carrier additives which may be present in the solubilizing compositions of the present invention include, but are not limited to: (1) emulsifiers, lubricants, surfactants, rheology modifiers, viscosity adjusters, foam stabilizers, and polymeric thickening agents; (2) pH adjusting agents and buffering agents designed to prevent age-induced changes in formula characteristics or surfactant degradation; and (3) specialty additives which impart improved organoleptic properties to the solubilizing composition and/or the treated hair (examples include fragrances, strengtheners, moisturizers, conditioning agents, proteins, re-fatting agents, anti-irritants, etc.). Such materials and the incorporation thereof into hair care products are generally well-known to one or ordinary skill in the art. Accordingly, except for the specific exemplary and non-limiting carrier additives described below, the incorporation of such additives is not discussed in detail herein.

For example, in one aspect an exemplary strengthener suitable for use in the instant invention is Soybean Oil. As one of skill in the art will appreciate, Soybean oil can soften and strengthen skin and/or hair to which it is applied. Further, soybean oil also exhibits moisturizing effects for the skin and hair as well. When used, a strengthener such as soybean oil can be present in an amount in the range of from 0 up to approximately 45 weight percent of the total composition, including such exemplary amounts as 5, 10, 15, 20, 25, 30, 35, or 40 weight percent, or even any amount in a range derived from these values. Exemplary soybean oils are commercially available from Columbus Foods Company, Chicago, Ill.

In still another aspect, carrot oil or carrot root extract can be added to the composition as an additive for conditioning and moisturizing dry hair and skin. An exemplary commercially available carrot oil product suitable for use as a carrier additive is the Crodarom Carrot O available from Croda, Inc. Crodarom Carrot O is an exemplary carrot root extract that is capable of conditioning and moisturizing rough, dried skin and or hair. Although a carrot oil or extract can be used in any desired amount, the carrot root extract is typically used in the present compositions in an amount ranging from approximately 0 to 0.5 weight percent of the total composition, including such exemplary amounts as 0.1, 0.2, 0.3, or 0.4 weight percent, or even any amount in a range derived from these values. Relatively low molecular weight polyethylene glycols can also be used as effective moisturizing agents. For example, PEG-75 Lanolin Oil, commercially available from Croda, Inc., is an exemplary polyethylene glycol moisturizer additive that can be used in the compositions of the present invention. While it can be present in any desired amount, polyethylene glycol moisturizing additives are in one aspect used in an amount in the range of from 0 to 5 weight percent of the total composition, including exemplary amounts of 1, 2, 3, or 4 weight percent of the total composition. Still further, a polyethylene glycol additive can also be present in any amount within a range derived from the above mentioned values.

One or more emulsifiers can also be included in the carrier composition as an optional carrier additive. For example, a polysorbate additive can optionally be used in the carrier composition as an emulsifier. As one of skill in the art will appreciate, an emulsifier such as polysorbate, can be incorporated into an aqueous based formulation to facilitate the coupling of water soluble components with water insoluble components. While an emulsifier can be present in any amount necessary to achieve the desired function, in one aspect an emulsifier can be present in the inventive compositions in an amount ranging from 0 to 10 weight percent based upon the total weight of the composition, including exemplary amounts of 1, 2, 3, 4, 5, 6, 7, 8 or even 9 weight percent. Still further an emulsifier can also be present in an amount within any range derived from the above mentioned values. Several polysorbate emulsifiers are commercially available, including for example, Polysorbate 20 and Polysorbate 80, commercially available from ICI, Americas, Inc., Bridgewater, N.J., under the trade name Tween® 20 and Tween® 80.

In still another aspect, the compositions of the present invention comprise a lubricant carrier additive such as, for example, cyclomethicone. Cyclomethicone is a silicone polymer that can aid in plasticizing the solubilizer composition. Additionally, cyclomethicone can also provide gloss and lubricity to the treated hair fiber. Still further, a lubricant such as cyclomethicone can also add lubricity to sprayer orifices of a pump to prevent any clogging, which can be particularly beneficial for use with solubilizer compositions that are formulated for spray on applications.

It should also be understood that the composition of the present invention can be provided in any desired compositional form. For example, and without limitation, the solubilizer compositions of the present invention can be formulated as a spray, gel, cream, mousse, and the like. To this end, formulating hair care compositions as sprays, gels, creams, mousses, and the like is generally well-known to one or ordinary skill in the art and can therefore be obtained through routine experimentation. As such, the specific optimization and selection of the components suitable for providing spray, gel, cream, and mousse is not discussed in detail herein.

As briefly summarized above, it has been discovered that the compositions of the present invention can be used to solubilize a variety of hair styling aides, including without limitation, latex bonding agents and styling aides which contain fixative resins to obtain and maintain a desired hairstyle. In one aspect, the compositions of the present invention are especially well suited for use by consumers who use styling aides on a daily basis without shampooing between applications; use large quantities of resinous styling aides to obtain a desired style; have chemically-treated, dry or damaged hair; and/or use styling aides in conjunction with heat to obtain and maintain their desired hair style.

Still further, it has also been discovered that the use of these inventive compositions resulted in significantly less hair breakage, little or no drying effects on hair and scalp, little or no scalp irritation and, in some aspects, can actually prevent additional damage to the hair associated with the use of conventional stripping shampoos (cuticle lifting, hair swelling, etc) by eliminating the need for such shampoos. Hair treated with the compositions of the current invention not only experienced significantly less breakage during combing experiments, the hair was actually moisturized by the residual, non-toxic solvent left on the hair. The end result was hair with improved appearance and combability (combability refers to the relative amount of force required to pass a styling tool, such as a comb, through the hair assembly).

Accordingly, in another aspect, the present invention provides several methods for using the compositions of the present invention. For example, in one aspect, the compositions of the present invention can be used to provide an effective method for removing a hair styling agent from hair. For example, it has been discovered that the compositions of the present invention are suitable for solubilizing and removing hair bonding agents and, more particularly, hair-bonding agents comprised of latex. Alternatively, these compositions are also effective in solubilizing and removing residues of resinous styling gels, sprays, spritz, or mousses.

According to this aspect, hair having a styling agent applied thereto can be contacted with one or more applications of a styling agent solubilizer as described herein for a time sufficient to solubilize the styling agent. Upon application of an amount sufficient to coat the hair, the solubilizing composition can remain in contact with the hair for an amount of time in the range of from about 30 seconds up to about 20 minutes, including exemplary periods of about 1 minute, about 2 minutes, about 3 minutes, about 4 minutes, about 5 minutes, about 6 minutes, about 7 minutes, about 8 minutes, about 9 minutes, or even about 10 minutes. Once the composition has been in contact for a sufficient period of time and the hair styling agent has been at least substantially solubilized, the hair can then optionally be combed through to separate any fibers that may have been previously adhered to one another by the hair styling agent.

After combing through the hair to disrupt any adhesions between hair fibers, the solubilized styling agent can then be removed from the hair. In one aspect, the solubilized styling agent can be removed by one or more applications of a water rinse. Alternatively, the solubilized styling agent can be removed by one or more applications of a shampoo treatment.

Still further, in another aspect, the compositions of the present invention can also be used to provide a method for restyling hair having one or more styling agents previously applied thereto. Once again, the compositions of the present invention are well suited for solubilizing and facilitating the restyling of hair having a number of conventionally known hair styling agents previously applied thereto, including for example, latex bonding agents as well as residues of resinous styling gels, sprays, sprits, or mousses.

Similar to the method of removal described above, hair having a styling agent previously applied thereto can be contacted with one or more applications of a styling agent solubilizer as described herein for a time sufficient to solubilize the styling agent. Upon application of an amount sufficient to coat the hair, the solubilizing composition can remain in contact with the hair for an amount of time in the range of from about 30 seconds up to about 20 minutes, including exemplary periods of about 1 minute, about 2 minutes, about 3 minutes, about 4 minutes, about 5 minutes, about 6 minutes, about 7 minutes, about 8 minutes, about 9 minutes, or even about 10 minutes. Once the composition has been in contact for a sufficient period of time and the hair styling agent has been at least substantially solubilized, the hair can optionally be combed through to separate any fibers that may have been previously adhered to one another by the hair styling agent.

After combing through the hair to disrupt any adhesions between hair fibers, the treated hair having solubilized styling agent disposed thereon can then be restyled to a desired curl or configuration without requiring the prior removal of the solubilized hair styling agent from the hair. After the hair has been restyled to a desired configuration, the solubilized hair styling agent can be dried to at least substantially remove the solubilizing composition components and, consequently, to secure the hair in the new style or configuration.

In still another aspect, the compositions of the present invention can be used to treat dry, coarse, and/or damaged hair in need of treatment. In one aspect, the treatment can comprise moisturizing the hair. In another aspect, treatment can comprise softening of the hair. The treatment can be provided by applying a coating of the inventive compositions to the hair and allowing the applied coating to remain in place without rinsing or combing the treated hair for a period of time sufficient to at least substantially penetrate the hair and until the carrier has at least substantially evaporated. A heat source can also be used to complete the re-drying of any solubilized resinous hair styling aides that may be present on the treated hair. Without intending to be limited by theory, it is believed that residual solvent trapped inside the hair fibers can serve as a plasticizing agent which enhances moisture retention and refreshes the look of the treated hair. Still further, the residual solvent can also enhance the flexibility and body of the treated hair.

EXPERIMENTAL

The following Examples are put forth so as to provide those of ordinary skill in the art with a complete disclosure and description of how the compounds claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, ingredient parts are indicated as parts by weight, temperature is in ° F. or is at room temperature, and pressure is at or near atmospheric.

Examples 1-5: Hair Bonding Agent Remover

TABLE 1

Inventive Examples 1 through 5

| Ingredient | Ex. 1 | Ex. 2 | Ex. 3 | Ex. 4 | Ex. 5 |
|---|---|---|---|---|---|
| Water | 60.4 | 46.9 | 70.35 | 81.85 | 46.9 |
| Methyl Soyate | 15 | 20 | 10 | 5 | 0 |
| Soybean Oil | 15 | 20 | 10 | 5 | 40 |
| Polysorbate 80 | 6 | 6 | 3 | 1.5 | 6 |
| Fragrance | 0.60 | 0.90 | 0.45 | 0.45 | 0.90 |
| Rheocare ATC | 3.0 | 6.0 | 6.0 | 6.0 | 6.0 |
| Crodarom Carrot O | 0.0 | 0.2 | 0.2 | 0.2 | 0.2 |

The compositions set forth in Table 1 above were applied to a latex rubber patch which had cured on the forearm skin and hair for 4 hours. After application, the compositions were allowed to remain on the latex patch and surrounding skin for approximately 5 min. The latex patches treated with inventive examples 1-4 were easily removed with no hair pulling or pain. The control composition of Ex. 5 (containing no active solvent) was difficult to remove and caused a great deal of pain and hair loss. This evaluation was again repeated decreasing the application time from 5 minutes to 2.5 minutes. Once again, the latex patches treated with the compositions of Examples 1-4 were easily removed compared to the control but were slightly more difficult to remove relative to the initial 5-min application test.

Examples 6-8: Resinous Hair Styling Gel Remover

TABLE 2

Inventive Examples 6 through 8

| Ingredient | Ex. 6 | Ex. 7 | Ex. 8 |
|---|---|---|---|
| Dipropylene Glycol | 12.2 | 25 | 48.75 |
| Ethanol (80 proof) | 85.3 | 72.5 | 48.75 |
| PEG-75 Lanolin | 1.00 | 1.00 | 1.00 |
| Cyclomethicone | 0.1 | 0.1 | 0.1 |
| Fragrance | 0.40 | 0.40 | 0.40 |
| Polysorbate-20 | 1.0 | 1.0 | 1.0 |

Three inventive spray-type compositions, having the formulations set forth in Table 2 above, were prepared and tested for their ability to remove several commercially available resinous hair styling products set forth in Table 3 below.

TABLE 3

Commercially Available Resinous Styling Gels

| Sample | Product | Ingredients |
|---|---|---|
| A | Equate "Extra Hold" Styling Gel (Garcoa Labs; Calabras, CA) | Water, PVP, Sorbitol, Carbomer, Fragrance, Keratin amino acids, Panthenyl Ethyl Ether, Palmitoyl oligopeptide, Glyceryl polymethacrylate, Rahnelia/Soy protein ferment, PEG 8, PEG-75 lanolin, Propylene glycol, Glycerin, Oleth-20, Aminomethyl propanol, Potassium sorbate, Tetrasodium EDTA, Methyl paraben, Diazodinyl urea, Methylchloroisothiazolinone, Methylisothiazolinone, Benzophenone-4, D&C Red #33, Red #40. |
| B | Proclaim Crystal Ice (Beauty Labs, Inc.; Dallas, TX) | Water, Glycerin, Triethanolamine, PVP, Hydrolyzed keratin, Carbomer, DMDM hydantoin, Methyl paraben, Polysorbate-20, Fragrance. |

TABLE 3-continued

Commercially Available Resinous Styling Gels

| Sample | Product | Ingredients |
|---|---|---|
| C | Ampro Pro-style Protein Styling Gel (Ampro Industries; Memphis, TN) | Water Sodium salt of Carbomer 940, Hydrolyzed collagen, Propylene glycol, Imidazolidinyl urea, Methyl paraben, Propyl paraben, Caramel color, Fragrance. |
| D | Motions Foaming Wrap Lotion (Motions; Melrose Park, IL) | Water, Polyquaternium-11, SD alcohol 40, Cetrimonium chloride, TEA lauroyl collagen, Amino acids, Dimethicone copolyol, Panthenol, PEG-75 lanolin, Oleth-20, DMDM hydantoin, Fragrance. |
| E | Paul Mitchell Freeze and Shine Super Spray Firm Hold Finishing Spray (John Paul Mitchell Systems; Beverly Hills, CA) | SD alcohol 40, Water, Octylacrylamide/Acrylates/Butylaminoethyl methacrylate copolymer, Dimethicone, Bisamino hydroxypropyl copolyol/Algae/*Aloe barbadensis* leaf/*Anthemis Nobilis*/Henna/ *Simmondsia Chinensis*/*Rosmarnius Officinalis*/ Dimethicone copolyol, Panthenol, Benzophenone-3, Triethyl citrate, Cocamidopropyl betaine, Fragrance, Aminomethyl propanol. |
| F | Spiked Out Rock Hard Hold (Vogue International; Tampa, FL) | Deionized water, PVP/VA copolymer, Sorbitan isostearate, Vinyl caprolactam/PVP Dimethylaminoethyl methacrylate copolymer, Petrolatum, Triconinyl PVP, Glycerin, Hydroxyethyl cellulose, Steareth-2, Stearyl alcohol, Cetyl alcohol, Steareth-21, Corn starch modified, *Cochearia Armoracia*, Retinyl palmitate, Tocopheryl acetate, Ascorbyl acetate, *Coffea Arabica*, *Macrocystis Pyfera*, Caffeine, Iodopropynyl butylcarbamate, Diazodinyl urea, Propyl paraben, Methyl paraben, Disodium EDTA, Fragrance |
| G | Pump-it Up (Bronner Brothers; Atlanta, GA) | SDA 40 alcohol, PVM/MA copolymer, Cyclomethicone, Silk Protein, Panthenol, D&C Red 33, Fragrance |

The specific procedure used to evaluate the formulations of Examples 6, 7 and 8 were as follows. First, individual tresses of Light Brown European Hair (DeMeo Brothers Ltd.; New York), approximately 0.25 inch by 8 inches, were bound at the proximal end. Each tress was then thoroughly combed with a clean, fine-toothed comb to remove any loose or broken hairs before any further use. The commercial styling products were then applied to the tresses in a manner consistent with the manufacturers suggested usage. A total of three tresses were prepared for each product being evaluated. The tresses were then wound around a 1.0-inch diameter glass tube and secured with a plastic curler clip immediately after the application of the styling product. The tresses were then allowed to air dry at least 24 hours before testing.

One tress from each group of three was reserved as a control. The control tresses were combed through without the application of any other treatments. A second tress from each group of three was then treated with "gel remover" prototype consistent with the nature of the prototype (i.e., sprays were delivered from a fine-mist sprayer; gels were applied with fingertips, etc.). A time delay of 2.5 minutes was allowed before the treated tress was combed through with a fine-toothed comb. The third tress from each group of three was then treated with "gel remover" prototype consistent with the nature of the prototype. A time delay of 5.0 minutes was allowed before the treated tress was combed through with a fine-toothed comb.

During testing, every attempt was made to use consistent force during combing. To that end, each tress was combed through using 10 strokes with a fine-toothed comb. Additionally, the control tress was used to help minimize the effect of variables including, relative humidity, changes in combing force applied, and the like. After combing, broken hairs were collected and counted. The hair breakage data from these tests are set forth in Tables 4, 5 and 6 below:

TABLE 4

Effect of Spray-On Remover of Ex. 6 on Hair Breakage During Combing

| Tress # | Styling Product | Delay between application of remover and comb through | Number of broken hairs from comb through |
|---|---|---|---|
| 1 | B | Control | 18 |
| 2 | B | 2.5 min | 4 |
| 3 | B | 5.0 min | 1 |
| 4 | A | Control | 49 |
| 5 | A | 2.5 min | 7 |
| 6 | A | 5.0 min | 4 |
| 7 | C | Control | 31 |
| 8 | C | 2.5 min | 1 |
| 9 | C | 5.0 min | 1 |
| 10 | D | Control | 15 |
| 11 | D | 2.5 min | 1 |
| 12 | D | 5.0 min | 0 |
| 13 | E | Control | 46 |
| 14 | E | 2.5 min | 17 |
| 15 | E | 5.0 min | Not available* |
| 16 | F | Control | 25 |
| 17 | F | 2.5 min | 2 |
| 18 | F | 5.0 min | 0 |
| 19 | G | Control | 128 |
| 20 | G | 2.5 min | 12 |
| 21 | G | 5.0 min | 2 |

*Tress 15 was dropped and became wet with water before combing could begin.

TABLE 5

Effect of Spray-On Remover of Ex. 7 on Hair Breakage During Combing

| Tress # | Styling Product | Delay between application of remover and comb through | Number of broken hairs from comb through |
|---|---|---|---|
| 22 | B | Control | 50 |
| 23 | B | 2.5 min | 6 |
| 24 | B | 5.0 min | 2 |
| 25 | A | Control | 31 |
| 26 | A | 2.5 min | 12 |
| 27 | A | 5.0 min | 1 |
| 28 | C | Control | 91 |
| 29 | C | 2.5 min | 3 |
| 30 | C | 5.0 min | 2 |
| 31 | D | Control | 31 |
| 32 | D | 2.5 min | 3 |
| 33 | D | 5.0 min | 2 |
| 34 | E | Control | 63 |
| 35 | E | 2.5 min | 12 |
| 36 | E | 5.0 min | 14 |
| 37 | F | Control | 105 |
| 38 | F | 2.5 min | 3 |
| 39 | F | 5.0 min | 12 |
| 40 | G | Control | 283 |
| 41 | G | 2.5 min | 26 |
| 42 | G | 5.0 min | 28 |

TABLE 6

Effect of Spray-On Remover of Ex. 8 on Hair Breakage During Combing

| Tress # | Styling Product | Delay between application of remover and comb through | Number of broken hairs from comb through |
|---|---|---|---|
| 43 | B | Control | 58 |
| 44 | B | 2.5 min | 2 |
| 45 | B | 5.0 min | 2 |
| 46 | A | Control | 61 |
| 47 | A | 2.5 min | 2 |
| 48 | A | 5.0 min | 0 |
| 49 | C | Control | 64 |
| 50 | C | 2.5 min | 4 |
| 51 | C | 5.0 min | 3 |
| 52 | D | Control | 14 |
| 53 | D | 2.5 min | 1 |
| 54 | D | 5.0 min | 2 |
| 55 | E | Control | 96 |
| 56 | E | 2.5 min | 0 |
| 57 | E | 5.0 min | 0 |
| 58 | F | Control | 149 |
| 59 | F | 2.5 min | 1 |
| 60 | F | 5.0 min | 0 |
| 61 | G | Control | 166 |
| 62 | G | 2.5 min | ND** |
| 63 | G | 5.0 min | 0 |

**N/D means "not determined".
Tress was dropped and wet with water prior to combing.

A review of the data set forth in Tables 4, 5 and 6 indicates the each of the sampled inventive hair styling gel removers resulted in a decreased number of broken hairs after combing compared to the control tresses in each test. The reduction in broken hairs indicates that less damage to the tress occurred when the inventive compositions were used.

Examples 9-12

Four inventive spray-type compositions, having varying concentrations of dipropylene glycol as set forth in Table 7 below, were prepared and tested for their ability to remove the commercially available "Pump-it Up" resinous styling product from Table 3 above.

TABLE 7

Inventive Examples 9 through 12

| Ingredient | Ex. 9 | Ex. 10 | Ex. 11 | Ex. 12 |
|---|---|---|---|---|
| Dipropylene Glycol (Dow Chemical) | 25 | 12.5 | 9.375 | 6.25 |
| SD-40 Alcohol | 72.9 | 85.4 | 88.525 | 91.65 |
| PEG-75 Lanolin (50% in water) | 1 | 1 | 1 | 1 |
| Cyclomethicone | 0.1 | 0.1 | 0.1 | 0.1 |
| Coconut Melon Fragrance | 0.4 | 0.40 | 0.40 | 0.40 |
| Polysorbate-20 | 0.6 | 0.6 | 0.6 | 0.6 |

The specific procedure used to evaluate the formulations of Examples 9-12 were as follows. First, individual tresses of virgin 50% grey hair (DeMeo Brothers Ltd.; New York), approximately 0.25 inch by 8 inches, were bound at the proximal end. Two tresses were prepared for each sample formulation being evaluated. A ninth control tress was also prepared. Each tress was then thoroughly combed with a clean, fine-toothed comb to remove any loose or broken hairs before any further use. The Pump-it Up styling product was then applied to the nine tresses in a manner consistent with the manufacturers suggested usage. The tresses were then wound around a 1.0-inch diameter glass tube and secured with a plastic curler clip immediately after the application of the styling product. The tresses were then allowed to air dry at least 24 hours before testing.

The control tress was first combed through without the application of any other treatments. A first tress from each group of tresses designated for each sample formulation was then treated with the inventive spray composition of Examples 9-12, respectively. A time delay of 2.5 minutes was allowed before each treated tress was combed through with a fine-toothed comb. The second tress from each group of tresses designated for each sample formulation was then treated with the inventive spray composition of Examples 9-12, respectively. A time delay of 5.0 minutes was allowed before the second treated tresses were combed through with a fine-toothed comb.

During testing, every attempt was made to use consistent force during combing. To that end, each tress was combed through using 12 strokes with a fine-toothed comb. Additionally, the control tress was used to help minimize the effect of variables including, relative humidity, changes in combing force applied, and the like. After combing, broken hairs were collected and counted. The hair breakage data from these tests are set forth in Table 8 below:

TABLE 8

Effect of Examples 9 through 12 on Hair Breakage During Combing

| Tress # | Composition | Delay between application of remover and comb through | Number of broken hairs from comb through |
|---|---|---|---|
| 64 | Control | Control | 136 |
| 65 | Ex. 9 | 2.5 min | 11 |
| 66 | Ex. 10 | 2.5 min | 10 |
| 67 | Ex. 11 | 2.5 min | 32 |
| 68 | Ex. 12 | 2.5 min | 59 |
| 64 | Control | Control | 136 |
| 69 | Ex. 9 | 5.0 min | 0 |
| 70 | Ex. 10 | 5.0 min | 4 |
| 71 | Ex. 11 | 5.0 min | 35 |
| 72 | Ex. 12 | 5.0 min | 46 |

A review of the data set forth in Table 8 indicates that the inventive compositions of Examples 9, 10, 11, and 12 resulted in a decreased number of broken hairs after combing compared to the control tresses in each test. The reduction in broken hairs indicates that less damage to the tress occurred when the inventive compositions were used. Still further, the reduction in broken hairs resulted among varying concentrations of the dipropylene glycol.

Subjective evaluations of hair stickiness, ease of combing, and feel of treated tresses also yielded the following observations. There was a direct correlation between the ease of combing, residual stickiness, and after feel of the tresses and the amount of dipropylene glycol in the gel remover formula. Tresses treated with 25 wt % and 12.5 wt % dipropylene glycol were easier to comb, and had a softer, less sticky feel than the other tresses. The tress treated with the gel remover formula containing 25 wt % dipropylene glycol was also noticeably easier to comb, had no stickiness, and had a very good after feel. The tress treated with a gel remover containing 12.5 wt % dipropylene glycol was still easy to comb but there was more drag and some slight stickiness. The tresses treated with a gel remover containing 9.375 wt % dipropylene glycol were sticky and difficult to comb. The tress treated with 6.25 wt % dipropylene glycol was the most difficult to comb and the hair was extremely sticky. The time of application did not seem to affect the feel and combability of tresses treated with formulas containing 9.375 wt % and 6.25 wt % dipropylene glycol.

Examples 13-16

Four inventive spray-type compositions, having varying concentrations of dipropylene glycol in combination with water, as set forth in Table 9 below, were prepared and tested for their ability to remove the commercially available "Pump-it Up" resinous styling product from Table 3 above.

TABLE 9

Inventive Examples 13 through 16

| Ingredient | Ex. 13 | Ex. 14 | Ex. 15 | Ex. 16 | Control (b) |
|---|---|---|---|---|---|
| Dipropylene Glycol (Dow Chemical) | 25 | 12.5 | 9.375 | 6.25 | 0.0 |
| Water | 71.98 | 84.48 | 87.605 | 90.73 | 96.98 |
| Carbopol EDT 2020 | 0.35 | 0.35 | 0.35 | 0.35 | 0.35 |
| Methylparaben | 0.2 | 0.2 | 0.2 | 0.2 | 0.2 |
| Propylparaben | 0.1 | 0.1 | 0.1 | 0.1 | 0.1 |
| Cyclomethicone | 0.15 | 0.15 | 0.15 | 0.15 | 0.15 |
| Polysorbate-20 | 0.5 | 0.5 | 0.5 | 0.5 | 0.5 |
| TEA 99% | 0.32 | 0.32 | 0.32 | 0.32 | 0.32 |
| PEG-75 Lanolin (50% in water) | 1 | 1 | 1 | 1 | 1 |
| Coconut Melon Fragrance | 0.4 | 0.4 | 0.4 | 0.4 | 0.4 |

The specific procedure used to evaluate the formulations of Examples 13-16 were as follows. First, individual tresses of virgin 50% grey hair (DeMeo Brothers Ltd.; New York), approximately 0.25 inch by 8 inches, were bound at the proximal end. Two tresses were prepared for each inventive sample formulation being evaluated and also two tresses were prepared for the wet control (b) formulation comprising water without dipropylene glycol. An eleventh tress was also prepared for use as a dry control which received no remover formulation. Each tress was then thoroughly combed with a clean, fine-toothed comb to remove any loose or broken hairs before any further use. The Pump-it Up styling product was then applied to the eleven tresses in a manner consistent with the manufacturers suggested usage. The tresses were then wound around a 1.0-inch diameter glass tube and secured with a plastic curler clip immediately after the application of the styling product. The tresses were then allowed to air dry at least 24 hours before testing.

The dry control tress was first combed through without the application of any other treatments. A first tress from each group of remaining tresses designated for each sample formulation of examples 13 to 16 and for the wet control (b) formulation were treated with the respective formulations. A time delay of 2.5 minutes was allowed before each treated tress was combed through with a fine-toothed comb. The second tress from each group of tresses designated for each sample formulation of examples 13 to 16 and for the wet control (b) formulation were then treated with the respective formulations. A time delay of 5.0 minutes was allowed before the second treated tresses were combed through with a fine-toothed comb.

During testing, every attempt was made to use consistent force during combing. To that end, each tress was combed through using 12 strokes with a fine-toothed comb. Additionally, the control tress was used to help minimize the effect of variables including, relative humidity, changes in combing force applied, and the like. After combing, broken hairs were collected and counted. The hair breakage data from these tests are set forth in Table 10 below:

TABLE 10

Effect of Examples 13 through 16 on Hair Breakage During Combing

| Tress # | Composition | Delay between application of remover and comb through | Number of broken hairs from comb through |
|---|---|---|---|
| 73 | Dry Control | Control | 113 |
| 74 | Control (b) | 2.5 min | 88 |
| 75 | Ex. 13 | 2.5 min | 10 |
| 76 | Ex. 14 | 2.5 min | 11 |
| 77 | Ex. 15 | 2.5 min | 9 |
| 78 | Ex. 16 | 2.5 min | 22 |
| 73 | Dry Control | Control | 113 |
| 79 | Control (b) | 5.0 min | 58 |
| 80 | Ex. 13 | 5.0 min | 0 |
| 81 | Ex. 14 | 5.0 min | 2 |
| 82 | Ex. 15 | 5.0 min | 7 |
| 83 | Ex. 16 | 5.0 min | 32 |

Examples 17-19

TABLE 11

Styling Residue Remover Containing Tripropylene Glycol

| Ingredient | Ex. 17 | Ex. 18 | Ex. 19 |
|---|---|---|---|
| Tripropylene glycol (Dow Chemical) | 48.75 | 25.00 | 12.20 |
| Ethanol (80 proof) | 48.75 | 72.5 | 85.3 |
| PEG-75 Lanolin (Super Solan Flaked; Croda, Inc.) | 1.00 | 1.00 | 1.00 |
| Cyclomethicone | 0.10 | 0.10 | 0.10 |
| Melon fragrance | 0.40 | 0.40 | 0.40 |
| Polysorbate-20 | 1.00 | 1.00 | 1.00 |

The inventive compositions set forth in Table 10 above, containing tripropylene glycol as the active solvent, were prepared and evaluated for their ability to solubilize the commercially available fixative product Pump-it-Up, from Bonner Brothers (Atlanta, Ga.). The evaluation procedures set forth above and used to evaluate Examples 6-8 were followed. The data obtained from these tests are given in Table 12 below.

TABLE 12

Effect of Examples 17 through 19 on Hair Breakage During Combing

| Tress # | Composition | Delay between application of remover and comb through | Number of broken hairs from comb through |
|---|---|---|---|
| 84 | — | Control | 224 |
| 85 | Ex. 17 | 2.5 min | 28 |
| 86 | Ex. 17 | 5.0 min | 38 |
| 87 | — | Control | 281 |
| 88 | Ex. 18 | 2.5 min | 73 |
| 89 | Ex. 18 | 5.0 min | 14 |
| 90 | — | Control | 216 |
| 91 | Ex. 19 | 2.5 min | 67 |
| 92 | Ex. 19 | 5.0 min | 58 |

Once again, a review of the data set forth in Table 12 indicates that the inventive compositions of Examples 17, 18 and 19 resulted in a decreased number of broken hairs after combing compared to the control tresses in each test. The reduction in broken hairs indicates that less damage to the tress occurred when the inventive compositions were used.

Examples 20-22

TABLE 13

Styling Residue Remover Containing Methyl Soyate

| Ingredient | Ex. 20 | Ex. 21 | Ex. 22 |
|---|---|---|---|
| Methyl Soyate (Columbus Foods, Columbus, OH.) | 48.75 | 25.00 | 12.20 |
| Ethanol (80 proof) | 48.75 | 72.5 | 85.3 |
| PEG-75 Lanolin (Super Solan Flaked; Croda, Inc.) | 1.00 | 1.00 | 1.00 |
| Cyclomethicone | 0.10 | 0.10 | 0.10 |
| Melon fragrance | 0.40 | 0.40 | 0.40 |
| Polysorbate-20 | 1.00 | 1.00 | 1.00 |

The inventive compositions set forth in Table 13 above, containing methyl soyate as the active solvent, were prepared and evaluated for their ability to solubilize the commercially available fixative product Pump-it-Up, from Bonner Brothers. The evaluation procedures set forth above and used to evaluate Examples 6-8 were followed. The data obtained from these tests are given in Table 14 below.

TABLE 14

Effect of Examples 20 through 22 on Hair Breakage During Combing

| Tress # | Composition | Delay between application of remover and comb through | Number of broken hairs from comb through |
|---|---|---|---|
| 93 | — | Control | 266 |
| 94 | Ex. 20 | 2.5 min | 13 |
| 95 | Ex. 20 | 5.0 min | 23 |
| 96 | — | Control | 211 |
| 97 | Ex. 21 | 2.5 min | 52 |

TABLE 14-continued

Effect of Examples 20 through 22 on Hair Breakage During Combing

| Tress # | Composition | Delay between application of remover and comb through | Number of broken hairs from comb through |
|---|---|---|---|
| 98 | Ex. 21 | 5.0 min | 44 |
| 99 | — | Control | 237 |
| 100 | Ex. 22 | 2.5 min | 71 |
| 101 | Ex. 22 | 5.0 min | 63 |

A review of the data set forth in Table 14 indicates that the inventive compositions of Examples 20, 21, and 22 resulted in a decreased number of broken hairs after combing compared to the control tresses in each test. The reduction in broken hairs indicates that less damage to the tress occurred when the inventive compositions were used.

Example 23: Straightened Hair Without Removal of Styling Aid

A gel remover spray having the same composition as given in Example 7 was applied to the hair of a consumer whose hair contained heavy styling residues. The composition was left in place a period of time sufficient to loosen the residues (from 1 to 5 minutes generally) and the hair was combed through. A commercial hair-straightening system (Profectiv Anti-Damage Therapeutic relaxer; Strength of Nature; Savannah, Ga.) was used to effectively straighten the hair without the need for first rinsing or shampooing to remove the loosened styling residues. The treated hair was effectively straightened and no scalp irritation was noted.

Example 24: Restyled Curled Hair Without Removal of Styling Aid

A tress of DeMeo Light Brown European hair was treated with a commercially available fixative (Pump-It-Up; Bonner Brothers) and allowed to dry in a curled configuration. Gel remover spray composition containing approximately 15 wt % dipropylene glycol was applied to the hair and allowed to sit for 5 min. The tress was then combed through without damage. The excess gel-remover was blotted from the hair and the tress was curled in the opposite direction and locked into place by applying more commercial fixative. The resulting curl was more preferable to the previous in that it had a softer quality and more body.

What is claimed is:
1. A hair bonding agent remover composition comprising:
a) methyl soyate in an amount of from 5 weight percent to 20 weight percent, based on the total weight of the composition;
b) water in an amount of from 45 weight percent to 85 weight percent, based on the total weight of the composition;
(c) soybean oil in an amount of from 5 weight percent to 20 weight percent, based on the total weight of the composition; and
(d) polysorbate in an amount of from 1 weight percent to 9 weight percent, based on the total weight of the composition,
wherein the hair bonding agent remover is for applying to hair and removing a hair styling agent applied thereto.

2. The composition of claim 1, further comprising a fragrance.

* * * * *